United States Patent
Wu et al.

(10) Patent No.: US 8,198,068 B2
(45) Date of Patent: Jun. 12, 2012

(54) METHOD FOR STONEWASHING FABRICS USING CELLULASE

(75) Inventors: Guifang Wu, Beijing (CN); Sarah Teter, Menlo Park, CA (US); Paul Harris, Carnation, WA (US); Weijian Lai, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/811,533

(22) PCT Filed: Feb. 19, 2009

(86) PCT No.: PCT/CN2009/070471
§ 371 (c)(1),
(2), (4) Date: Jul. 2, 2010

(87) PCT Pub. No.: WO2009/103237
PCT Pub. Date: Aug. 27, 2009

(65) Prior Publication Data
US 2010/0287713 A1 Nov. 18, 2010

Related U.S. Application Data

(60) Provisional application No. 61/029,665, filed on Feb. 19, 2008.

(51) Int. Cl.
*D06M 16/00* (2006.01)
*C09B 67/00* (2006.01)
*C12N 9/62* (2006.01)

(52) U.S. Cl. .............................. 435/263; 8/401; 435/225

(58) Field of Classification Search ....................... None
See application file for complete search history.

(56) References Cited

FOREIGN PATENT DOCUMENTS

| WO | WO 91/17243 | 11/1991 |
|---|---|---|
| WO | WO 94/21801 | 9/1994 |
| WO | WO 95/09225 | 4/1995 |
| WO | WO 95/16782 | 6/1995 |
| WO | WO 97/15660 | 5/1997 |
| WO | WO 98/28410 | 7/1998 |
| WO | WO 98/45395 | 10/1998 |
| WO | WO 99/31255 | 6/1999 |
| WO | WO 00/14208 A1 | 3/2000 |
| WO | WO 02/12464 A2 | 2/2002 |
| WO | WO 2007/057418 | 5/2007 |

OTHER PUBLICATIONS

Fedorova et al., EMBL Database, Accession No. BOYB66 (2008).
Neirman et al., EMBL Database, Accession No. Q4WGT4 (2005).
William et al., Nature, vol. 438, No. 22-29, pp. 1151-1155 (2005).
Fowler et al., Geneseq Database, Accession No. AAY84329 (2000).
Mitchison et al., Geneseq Database, Accession No. AAU77416 (2002).
Dyck et al., IEEE, pp. 1508-1512 (1997).

*Primary Examiner* — Tekchand Saidha
*Assistant Examiner* — Md. Younus Meah
(74) *Attorney, Agent, or Firm* — Elias Lambiris (57) ABSTRACT

A method of forming localized variation of color density in the surface of a dyed cellulosic fabric with reducing back staining, with a composition comprising a cellulose having the amino acid sequence of SEQ ID NO: 2 or an amino acid sequence having at least 75% sequence identity with SEQ ID NO: 2 is provided. A method for biopolishing a cellulose-containing fabric by using the new endoglucanase is also provided.

18 Claims, 3 Drawing Sheets

SEQUENCE LISTING

<160> NUMBER OF SEQ ID NOS: 6

<210> SEQ ID NO 1
<211> LENGTH: 805
<212> TYPE: DNA
<213> ORGANISM: Aspergillus Funigatus

<400> SEQUENCE: 1

```
atgaagacct ttgcgatcct tggagctttc ttctcctctg ccctcgctca aactctctgt      60
gaccagtatg ccacctacag caacggccgc tacaccgtca acaacaacct ctggggcatg     120
agctctggct ccggctccca atgcacctat gtcgatagta tctccaactc gggcgtagcc     180
tggcatacga cctggacgtg gtccggcggc gacaaccagg tcaaaagcta cgccaactct     240
caggtctccc tgactaagaa gcttgtcagc cagatcagca gtatccccac caccgtgcag     300
tggagctatg ataataccaa cacccgcgcc gacgtcgcgt acgatctgtt cacagctgcg     360
gatcccaacc atgtcaccta cagcggggat tatgaactga tgatctggta tgagattgcg     420
ttattcatgt cggactggat ggctttcgct gattggcata ggctcgcccg ctacgggaac     480
gtccaaccca tcggctcgca gatcgccagt gtcaacattg gcggccataa ctgggagctg     540
tggtacggcg gcagcaccca gaagacgtac agctttgtct cggccacccc gatcacctcc     600
ttcagtggca atgtcatgga cttctggaac tatctgacca gaaatcatgg atacctgct     660
```

```
tcgagccagt acctgatcag tacgtccgcc acctcacctt gctcgagcgc cactgactag    720
tgcagatatg caattcggga ctgagccgtt cactggcggc cctgccacct tgacagtgtc    780
gcagtggacc gccagtgtga actaa                                          805
```

<210> SEQ ID NO 2
<211> LENGTH: 218
<212> TYPE: PRT
<213> ORGANISM: Aspergillus fumigatus
<220> FEATURE:
<221> NAME/KEY: mat_peptide
<222> LOCATION: (1)..(218)

<400> SEQUENCE: 2

```
Gln Thr Leu Cys Asp Gln Tyr Ala Thr Tyr Ser Asn Gly Arg Tyr Thr
1               5                   10                  15

Val Asn Asn Asn Leu Trp Gly Met Ser Ser Gly Ser Gly Ser Gln Cys
            20                  25                  30

Thr Tyr Val Asp Ser Ile Ser Asn Ser Gly Val Ala Trp His Thr Thr
        35                  40                  45

Trp Thr Trp Ser Gly Gly Asp Asn Gln Val Lys Ser Tyr Ala Asn Ser
    50                  55                  60

Gln Val Ser Leu Thr Lys Lys Leu Val Ser Gln Ile Ser Ser Ile Pro
65                  70                  75                  80

Thr Thr Val Gln Trp Ser Tyr Asp Asn Thr Asn Thr Arg Ala Asp Val
                85                  90                  95

Ala Tyr Asp Leu Phe Thr Ala Ala Asp Pro Asn His Val Thr Tyr Ser
            100                 105                 110

Gly Asp Tyr Glu Leu Met Ile Trp Leu Ala Arg Tyr Gly Asn Val Gln
        115                 120                 125

Pro Ile Gly Ser Gln Ile Ala Ser Val Asn Ile Gly Gly His Asn Trp
    130                 135                 140

Glu Leu Trp Tyr Gly Gly Ser Thr Gln Lys Thr Tyr Ser Phe Val Ser
145                 150                 155                 160

Ala Thr Pro Ile Thr Ser Phe Ser Gly Asn Val Met Asp Phe Trp Asn
                165                 170                 175

Tyr Leu Thr Arg Asn His Gly Tyr Pro Ala Ser Ser Gln Tyr Leu Ile
            180                 185                 190

Asn Met Gln Phe Gly Thr Glu Pro Phe Thr Gly Gly Pro Ala Thr Leu
        195                 200                 205

Thr Val Ser Gln Trp Thr Ala Ser Val Asn
    210                 215
```

<210> SEQ ID NO 3
<211> LENGTH: 35
<212> TYPE: DNA
<213> ORGANISM: Artificial sequence
<220> FEATURE:
<223> OTHER INFORMATION: Synthetic construct

<400> SEQUENCE: 3

```
actggattta ccatgaagac ctttgcgatc cttgg                                35
```

<210> SEQ ID NO 4
<211> LENGTH: 32
<212> TYPE: DNA
<213> ORGANISM: Artificial sequence
<220> FEATURE:
<223> OTHER INFORMATION: Synthetic construct

<400> SEQUENCE: 4

```
agtcacctct agttagttca cactggcggt cc                                    32

<210> SEQ ID NO 5
<211> LENGTH: 21
<212> TYPE: DNA
<213> ORGANISM: Artificial sequence
<220> FEATURE:
<223> OTHER INFORMATION: Synthetic construct

<400> SEQUENCE: 5
ccacacttct cttccttcct c                                                21

<210> SEQ ID NO 6
<211> LENGTH: 21
<212> TYPE: DNA
<213> ORGANISM: Artificial sequence
<220> FEATURE:
<223> OTHER INFORMATION: Synthetic construct

<400> SEQUENCE: 6
ccccatcctt taactatagc g                                                21
```

METHOD FOR STONEWASHING FABRICS USING CELLULASE

CROSS-REFERENCE TO RELATED APPLICATIONS

This application is a 35 U.S.C. 371 national application of PCT/CN2009/070471 filed Feb. 19, 2009, which claims priority or the benefit under 35 U.S.C. 119 of U.S. provisional application No. 61/029,665 filed Feb. 19, 2008, the contents of which are fully incorporated herein by reference.

TECHNICAL FIELD

This invention relates to a method of forming localized variation of color density in the surface of a dyed cellulosic fabric with a composition comprising a new endoglucanase derived from *Aspergillus fumigatus* in terms of abrasion boosting and backstaining control. The present application also relates to a method for biopolishing a cellulose-containing fabric by using the new endoglucanase.

TECHNICAL BACKGROUND

In the manufacture of garments from dyed cellulosic fabric, e.g., blue jeans from indigo-dyed denim, it is common to treat the denim so as to provide a "stone-washed" look (localized abrasion of the color in the denim surface). Performance of endoglucanase on denim is strongly believed to depend on the structure and chemical nature of the enzyme.

In denim biostoning, abrasion and backstain of indigo are the two key performance indicators for a given endoglucanase. It is rare for a single endoglucanase to both provide high abrasion of denim and control indigo backstain to an acceptable level. The interaction between endoglucanase-indigo, endoglucanase-cellulose, and application pH's also contribute to denim abrasion and indigo backstain.

WO 98/45395 describes detergent compositions employed in low water wash processes. WO 97/15660 describes a method for preparing a crystalline endoglucanase enzyme. WO 95/16782 describes a novel truncated endoglucanase protein from *Trichoderma longibrachiatum* in reduced redeposition (backstaining) of dye onto the fabric while maintaining an equivalent level of abrasion.

WO 91/17243 and WO 95/09225 (Novo Nordisk) describe a process using a single-component endoglucanase denoted EGV with a molecular weight of 43 kD derived from *Humicola insolens* strain DSM 1800. WO 94/21801 (Genencor) describes the use in "stone washing" of a single-component endoglucanase called EGIII derived from *Trichoderma longibrachiatum*. WO 95/16782 (Genencor International) suggests the use of other single-component endoglucanases derived from *Trichoderma* in "stone washing".

A general problem in known "stone washing" methods is that of backstaining, i.e., a phenomenon whereby dye already removed by abrasion deposits on parts of the fabric or garment so as to even out the desired variation of color density or to discolor any light-colored parts of the garment. There is a need in the art for new endoglucanases that have good performance in denim abrasion.

SUMMARY OF THE INVENTION

We have surprisingly found that an endoglucanase derived from *Aspergillus fumigatus* has very good performance in stone-washing while reducing backstaining.

Accordingly, one aspect of the invention provides a method of forming localized variation of color density in the surface of a dyed cellulosic fabric, comprising contacting said fabric with a composition comprising a endoglucanase, wherein said endoglucanase has the amino acid sequence of SEQ ID NO:1 or an amino acid sequence having at least 70% sequence identity with SEQ ID NO:1.

Preferably, the fabric is indigo dyed denim.

Preferably, the endoglucanase is derived from an *Aspergillus* strain, preferably *Aspergillus fumigatus*.

Another aspect of the invention provides a method for reducing back-staining during the stonewashing of colored fabrics, which method comprises contacting the fabrics with a composition comprising a endoglucanase having the amino acid sequence of SEQ ID NO:1 or an amino acid sequence having at least 70% sequence identity with SEQ ID NO:1.

DETAILED DESCRIPTION OF THE INVENTION

Definitions

In this specification with claims, the following definitions apply:

The term "endoglucanase activity" is defined herein as an endo-1,4-beta-D-glucan 4-glucanohydrolase (E.C. No. 3.2.1.4) which catalyses the endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. For purposes of the present invention, endoglucanase activity is determined using carboxymethyl cellulose (CMC) hydrolysis according to the procedure of Ghose, 1987, Pure and Appl. Chem. 59: 257-268. One unit of endoglucanase activity is defined as 1.0 mmole of reducing sugars produced per minute at 50° C., pH 4.8.

In a preferred aspect, the polypeptides of the present invention having endoglucanase activity further have enzyme activity toward one or more substrates selected from the group consisting of xylan, xyloglucan, arabinoxylan, 1,4-beta-D-mannan, and galactomannan. The activity of the polypeptides having endoglucanase activity on these polysaccharide substrates is determined as percent of the substrate hydrolyzed to reducing sugars after incubating the substrate (5 mg per ml) with a polypeptide having endoglucanase activity of the present invention (5 mg protein per g of substrate) for 24 hours with intermittent stirring at pH 5.0 (50 mM sodium acetate) and 50° C. Reducing sugars in hydrolysis mixtures are determined by the p-hydroxybenzoic acid hydrazide (PHBAH) assay.

In a more preferred aspect, the polypeptides of the present invention having endoglucanase activity further have enzyme activity toward xylan. In another more preferred aspect, the polypeptides of the present invention having endoglucanase activity further have enzyme activity toward xyloglucan. In another more preferred aspect, the polypeptides of the present invention having endoglucanase activity further have enzyme activity toward arabinoxylan. In another more preferred aspect, the polypeptides of the present invention having endoglucanase activity further have enzyme activity toward 1,4-beta-D-mannan. In another more preferred aspect, the polypeptides of the present invention having endoglucanase activity further have enzyme activity toward galactomannan. In another more preferred aspect, the polypeptides of the present invention having endoglucanase activity further have enzyme activity toward xylan, xyloglucan, arabinoxylan, 1,4-beta-D-mannan, and/or galactomannan.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the endoglucanase activity of mature polypeptide of SEQ ID NO: 2.

Endoglucanases are classified into families on the basis of amino-acid sequence similarities according to the classification system described in Henrissat, B. et al.: Biochem. J., (1991), 280, p. 309-16, and Henrissat, B. et al.: Biochem. J., (1993), 293, p. 781-788.

The endoglucanases used in this invention are preferably single components, i.e., the aqueous medium used in the invention should be free of other endoglucanase components than those specified. Single component enzymes can be prepared economically by recombinant DNA technology, i.e., they can be produced by cloning of a DNA sequence encoding the single component, subsequently transforming a suitable host cell with the DNA sequence and expressing the component in the host.

Accordingly, the DNA sequence encoding a useful cellulase may be isolated by a general method involving cloning, in suitable vectors, a DNA library, e.g., from one of the microorganisms indicated later in this specification, transforming suitable yeast host cells with said vectors, culturing the host cells under suitable conditions to express any enzyme of interest encoded by a clone in the DNA library, screening for positive clones by determining any cellulase activity of the enzyme produced by such clones, and isolating the enzyme encoding DNA from such clones.

The general method is further disclosed in WO 94/14953 (Novo Nordisk) the contents of which are hereby incorporated by reference.

The DNA sequence coding for a useful endoglucanase may, for instance, be isolated by screening a cDNA library of the microorganism in question and selecting for clones expressing the appropriate enzyme activity (i.e., endoglucanase activity).

A DNA sequence coding for a homologous enzyme, i.e., an analogous DNA sequence, may be obtainable from other microorganisms. For instance, the DNA sequence may be derived by similarly screening a cDNA library of another fungus, such as a strain of an *Aspergillus* sp., in particular a strain of *A. aculeatus* or *A. niger*, a strain of *Trichoderma* sp., in particular a strain of *T. reesei, T. viride, T. longibrachiatum,* *T. harzianum* or *T. koningii* or a strain of a *Neocallimastix* sp., a *Piromyces* sp., a *Penicillium* sp., an *Agaricus* sp., or a *Phanerochaete* sp.

Alternatively, the DNA coding for a useful cellulase may, in accordance with well-known procedures, conveniently be isolated from DNA from a suitable source, such as any of the above-mentioned organisms, by use of synthetic oligonucleotide probes prepared on the basis of a known DNA sequence.

The DNA sequence may subsequently be inserted into a recombinant expression vector. This may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated.

In the vector, the DNA sequence encoding the endoglucanase should be operably connected to a suitable promoter and terminator sequence. The promoter may be any DNA sequence that shows transcriptional activity in the host cell of choice and may be derived from genes encoding proteins either homologous or heterologous to the host cell. The procedures used to ligate the DNA sequences coding for the endoglucanase, the promoter and the terminator, respectively, and to insert them into suitable vectors are well known to persons skilled in the art (cf., for instance, Sambrook et al., Molecular Cloning. A Laboratory Manual, Cold Spring Harbor, N.Y., 1989).

The host cell that is transformed with the DNA sequence is preferably a eukaryotic cell, in particular a fungal cell such as a yeast or filamentous fungal cell. In particular, the cell may belong to a species of *Aspergillus* or *Trichoderma*, most preferably *Aspergillus oryzae* or *Aspergillus niger*. Fungal cells may be transformed by a process involving protoplast formation and transformation of the protoplast followed by regeneration of the cell wall in a manner known per se. The use of *Aspergillus* as a host microorganism is described in EP 238 023 (Novo Nordisk AS), the contents of which are hereby incorporated by reference. The host cell may also be a yeast cell, e.g., a strain of *Saccharomyces*, in particular *Saccharomyces cerevisiae*, or *Saccharomyces uvarum*, a strain of *Schizosaccharomyces* sp., such as *Schizosaccharomyces pombe*, a strain of *Hansenula* sp., *Pichia* sp., *Yarrowia* sp. such as *Yarrowia lipolytica*, or *Kluyveromyces* sp. such as *Kluyveromyces lactic.*

In the present context, the term "homologous" or "homologous sequence" is intended to indicate an amino acid sequence differing from those shown in each of the sequence listings shown hereinafter, respectively, by one or more amino acid residues.

The homologous sequence may be one resulting from modification of an amino acid sequence shown in these listings, e.g., involving substitution of one or more amino acid residues at one or more different sites in the amino acid sequence, deletion of one or more amino acid residues at either or both ends of the enzyme or at one or more sites in the amino acid sequence, or insertion of one or more amino acid residues at one or more sites in the amino acid sequence.

However, as will be apparent to the skilled person, amino acid changes are preferably of a minor nature, that is conservative amino acid substitutions that do not significantly affect the folding or activity of the protein, small deletions, typically of one to about 30 amino acids; small amino- or carboxylterminal extensions, such as an aminoterminal methionine residue, a small linker peptide of up to about 20-25 residues, or a small extension that facilitates purification, such as a poly-histidine tract, an antigenic epitope or a binding domain. See in general Ford et al., *Protein Expression and Purification* 2: 95-107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will also be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244: 1081-1085, 1989). In the latter technique mutations are introduced at every residue in the molecule, and the resultant mutant molecules are tested for biological (i.e., endoglucanase) activity to identify amino acid residues that are critical to the activity of the molecule.

Sites of substrate-enzyme interaction can also be determined by analysis of crystal structure as determined by such techniques as nuclear magnetic resonance, crystallography or photoaffinity labeling. See, for example, de Vos et al., *Science* 255: 306-312, 1992; Smith et al., *J. Mol. Biol.* 224: 899-904, 1992; Wlodaver et al., *FEBS Lett.* 309: 59-64, 1992.

The modification of the amino acid sequence may suitably be performed by modifying the DNA sequence encoding the enzyme, e.g., by site-directed or by random mutagenesis or a combination of these techniques in accordance with well-known procedures. Alternatively, the homologous sequence may be one of an enzyme derived from another origin than the endoglucanases corresponding to the amino acid sequences shown in each of the sequence listings shown hereinafter, respectively. Thus, "homologue" may, e.g., indicate a polypeptide encoded by DNA which hybridizes to the same probe as the DNA coding for the endoglucanase with the amino acid sequence in question under certain specified conditions (such as presoaking in 5×SSC and prehybridising for 1 h at 400° C. in a solution of 20% formamide, 5×Denhardt's solution, 50 mM sodium phosphate, pH 6.8, and 50 mg of denatured sonicated calf thymus DNA, followed by hybridization in the same solution supplemented with 100 mM ATP for 18 hours at 400° C.). The homologous sequence will normally exhibit a degree of identity of at least 50%, such as at least 60%, 65%, 70%, 75%, 80%, 85%, 90% or even 95% with the amino acid sequences shown in each of the sequence listings shown hereinafter, respectively.

The term "identity" is define herein as the relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Dyed Cellulosic Fabric

The process of the invention may be applied to any type of dyed cellulosic fabric where it is desired to form localized variation of color density in the surface. An example of particular commercial interest is denim, particularly indigo-dyed denim for use in blue jeans, etc.

The fabric may be treated in the form of unsewn fabric or a sewn garment made of such fabric. It is of particular interest to apply the process of the invention to a new, clean fabric or garment.

Process Conditions

The process of the invention may be carried out at conventional conditions in a washing machine conventionally used for stone-washing (e.g., a washer-extractor).

Typical conditions are a temperature of 25-60° C. and a fabrics: liquor ratio from 1:3 to 1:20 for 15 minutes to 2 hours. Optionally, conventional additives may be used, e.g., a buffer, a surfactant (anionic and/or non-ionic, such as PW100i) and/or a polymer (such as PVP, polyacrylate and polyacrylamide).

EXAMPLES

Examples 1-5 demonstrate the preparation of *Aspergillus niger* genetically engineered so as to be capable of producing the endoglucanase of present invention or so as to produce specific endoglucanase according to the requirement of present invention.

Materials

Chemicals used as buffers and substrates were commercial products of at least reagent grade.

Strains

*Aspergillus oryzae* Jal250 strain (WO 99/61651) was used for expression of the *Aspergillus fumigatus* cel12a gene. *Aspergillus fumigatus* PaHa34 was used as the source of the cel12a gene encoding a glycosyl hydrolase Family 12 endoglucanase.

Media

Potato dextrose medium was composed per liter of 39 grams of potato dextrose (Difco).

PDA plates were composed per liter of 39 grams of potato dextrose agar.

MDU2BP medium was composed per liter of 45 g of maltose, 1 g of $MgSO_4 \cdot 7H_2O$, 1 g of NaCl, 2 g of $K_2SO_4$, 12 g of $KH_2PO_4$, 7 g of yeast extract, 2 g of urea, and 0.5 ml of AMG trace metals solution, pH to 5.0.

AMG trace metals solution was composed per liter of 14.3 g of ZnSO$_4$.7H$_2$O, 2.5 g of CuSO$_4$.5H$_2$O, 0.5 g of NiCl$_2$.6H$_2$O, 13.8 g of FeSO$_4$.7H$_2$O, 8.5 g of MnSO$_4$.H$_2$O, and 3 g of citric acid.

YEG medium was composed per liter of 5 grams of yeast extract and 20 grams of dextrose.

Example 1

Cloning of the Cel12a Gene and Construction of an Aspergillus oryzae Expression Vector Two synthetic oligonucleotide primers shown below were designed to PCR amplify a Aspergillus fumigatus gene encoding a glycosyl hydrolase Family 12 endoglucanase (CEL12A) from the genomic DNA prepared as described in WO 03/012071. An InFusion Cloning Kit (BD Biosciences, Palo Alto, Calif., USA) was used to clone the fragment directly into the expression vector, pAILo2, without the need for restriction digests and ligation.

```
Forward primer:
                                          (SEQ ID NO: 3)
5'- ACTGGATTTACCATGAAGACCTTTGCGATCCTTGG -3'

Reverse primer:
                                          (SEQ ID NO: 4)
5'- AGTCACCTCTAGTTAGTTCACACTGGCGGTCC -3'
```

Bold letters represent coding sequence. The remaining sequence is homologous to the insertion sites of pAILo2.

Seventy-five picomoles of each of the primers above were used in a PCR reaction containing 120 ng of Aspergillus fumigatus genomic DNA, 1×Pfx Amplification Buffer (Invitrogen, Carlsbad, Calif., USA), 1.5 μl of 10 mM blend of dATP, dTTP, dGTP, and dCTP, 1.9 units of Platinum Pfx DNA Polymerase (Invitrogen, Carlsbad, Calif., USA), and 1 μl of 50 mM MgSO$_4$ in a final volume of 50 μl. The amplification conditions were one cycle at 94° C. for 2 minutes; 30 cycles each at 94° C. for 15 seconds, 55° C. for 30 seconds, and 68° C. for 1.5 minutes.

The reaction products were isolated on a 1.0% agarose gel using 40 mM Tris base-20 mM sodium acetate-1 mM disodium EDTA (TAE) buffer where a 0.9 kb product band was excised from the gel and purified using a QIAQUICK® Gel Extraction Kit (QIAGEN Inc., Valencia, Calif., USA) according to the manufacturer's instructions.

Figure 1:
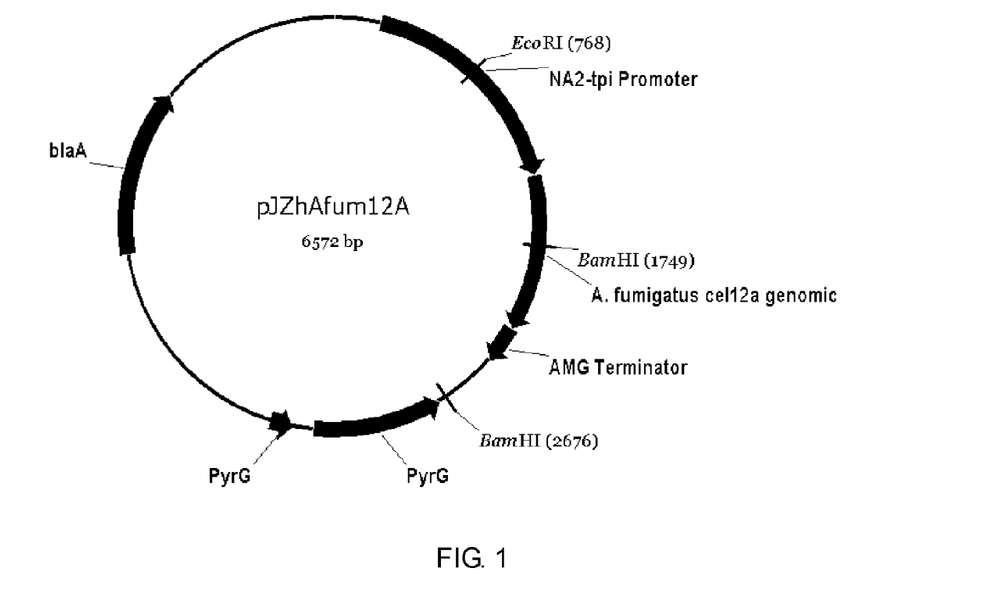
FIG. 1 shows an outline of the construction of expression plasmid of pJZhAfum12A.

The fragment was then cloned into the pAILo2 expression vector using an Infusion Cloning Kit. The vector was digested with restriction endonucleases Nco I and Pac I (using conditions specified by the manufacturer). The fragment was purified by gel electrophoresis and QIAQUICK® gel purification. The gene fragment and the digested vector were fused together in a reaction resulting in the expression plasmid pJZhAfum12A (FIG. 1) in which transcription of the cel12a gene was under the control of the NA2-tpi promoter. The fusion reaction (50 μl) was composed of 1× InFusion Buffer (BD Biosciences, Palo Alto, Calif., USA), 1×BSA (BD Biosciences, Palo Alto, Calif., USA), 1 μl of Infusion enzyme (diluted 1:10) (BD Biosciences, Palo Alto, Calif., USA), 150 ng of pAILo2 digested with Nco I and Pac I, and 25 ng of the Aspergillus fumigatus cel12a purified PCR product. The reaction was incubated at room temperature for 30 minutes. One μl of the reaction was used to transform E. coli XL10 Solopac Gold cells (Stratagene, La Jolla, Calif., USA). Plasmid DNA was prepared from one transformant using a BIOROBOT® 9600 (QIAGEN Inc., Valencia, Calif., USA) and the identity verified by DNA sequencing.

Example 2

Characterization of the Aspergillus fumigatus Genomic Sequence Encoding a Cel12A Endoglucanase DNA sequencing of the Aspergillus fumigatus cel12a gene from pJZhAfum12A was performed with a Perkin-Elmer Applied Biosystems Model 377 XL Automated DNA Sequencer (Perkin-Elmer/Applied Biosystems, Inc., Foster City, Calif., USA) using dye-terminator chemistry (Giesecke et al., 1992, Journal of Virology Methods 38: 47-60). Nucleotide sequence data were scrutinized for quality and all sequences were compared to each other with assistance of PHRED/PHRAP software (University of Washington, Seattle, Wash.).

A gene model for the Aspergillus fumigatus sequence was constructed based on a full-length cDNA sequence obtained previously. The nucleotide sequence (SEQ ID NO: 1) and deduced amino acid sequence (SEQ ID NO: 2) are shown below The genomic fragment of 805 bp (including stop codon) encodes a polypeptide of 234 amino acids, interrupted by 2 introns of 54 and 46 bp. The % G+C content of the gene is 56.2%. Using the SignalP software program (Nielsen et al., 1997, Protein Engineering 10:1-6), a signal peptide of 16 residues was predicted. The predicted mature protein contains 218 amino acids with a molecular mass of 24.1 kDa.

```
ATGAAGACCTTTGCGATCCTTGGAGCTTTCTTCTCCTCTGCCCTCGCTCAAACTCTCTGTGACCAGTATGCCACCTACAGC    81
 M  K  T  F  A  I  L  G  A  F  F  S  S  A  L  A  Q  T  L  C  D  Q  Y  A  T  Y  S

AACGGCCGCTACACCGTCAACAACAACCTCTGGGGCATGAGCTCTGGCTCCGGCTCCCAATGCACCTATGTCGATAGTATC    162
 N  G  R  Y  T  V  N  N  N  L  W  G  M  S  S  G  S  G  S  Q  C  T  Y  V  D  S  I

TCCAACTCGGGCGTAGCCTGGCATACGACCTGGACGTGGTCCGGCGGCGACAACCAGGTCAAAAGCTACGCCAACTCTCAG    243
 S  N  S  G  V  A  W  H  T  T  W  T  W  S  G  G  D  N  Q  V  K  S  Y  A  N  S  Q

GTCTCCCTGACTAAGAAGCTTGTCAGCCAGATCAGCAGTATCCCCACCACCGTGCAGTGGAGCTATGATAATACCAACACC    324
 V  S  L  T  K  K  L  V  S  Q  I  S  S  I  P  T  T  V  Q  W  S  Y  D  N  T  N  T

CGCGCCGACGTCGCGTACGATCTGTTCACAGCTGCGGATCCCAACCATGTCACCTACAGCGGGGATTATGAACTGATGATC    405
 R  A  D  V  A  Y  D  L  F  T  A  A  D  P  N  H  V  T  Y  S  G  D  Y  E  L  M  I

TGGTATGAGATTGCGTTATTCATGTCGGACTGGATGGCTTTCGCTGATTGGCATAGGCTCGCCCGCTACGGGAACGTCCAA    486
 W                                                     L  A  R  Y  G  N  V  Q
```

```
                                                                                     -continued
CCCATCGGCTCGCAGATCGCCAGTGTCAACATTGGCGGCCATAACTGGGAGCTGTGGTACGGCGGCAGCACCCAGAAGACG   567
 P   I   G   S   Q   I   A   S   V   N   I   G   G   H   N   W   E   L   W   Y   G   G   S   T   Q   K   T TACAGCTTTGTCTCGGCCACCCCGATCACCTCCTTCAGTGGCAATGTCATGGACTTCTGGAACTATCTGACCAGAAATCAT   648
 Y   S   F   V   S   A   T   P   I   T   S   F   S   G   N   V   M   D   F   W   N   Y   L   T   R   N   H GGATACCCTGCTTCGAGCCAGTACCTGATCAGTACGTCCGCCACCTCACCTTGCTCGAGCGCCACTGACTAGTGCAGATAT   729
 G   Y   P   A   S   S   Q   Y   L   I                                                                 N   M GCAATTCGGGACTGAGCCGTTCACTGGCGGCCCTGCCACCTTGACAGTGTCGCAGTGGACCGCCAGTGTGAATAA         805
 Q   F   G   T   E   P   F   T   G   G   P   A   T   L   T   V   S   Q   W   T   A   S   V   N
```

Nucleic acid sequence and translation of the coding region of the cel12a gene of *Aspergillus fumigatus*. Introns are shown italicized and the predicted signal peptide is underlined.

MKTFAILGAFFSSALAQTLCDQYATYSNGRYTVNNNLWGMSSGSGSQC

TYVDSISNSGVAWHTTWTWSGGDNQVKSYANSQVSLTKKLVSQISSIP

TTVQWSYDNTNTRADVAYDLFTAADPNHVTYSGDYELMIWLARYGNVQ

PIGSQIASVNIGGHNWELVVYGGSTQKTYSFVSATPITSFSGNVMDFW

NYLTRNHGYPASSQYLINMQFGTEPFTGGPATLTVSQWTASVN

Amino acid sequence of the CEL12A pre-polypeptide of *Aspergillus fumigatus*.

QTLCDQYATYSNGRYTVNNNLWGMSSGSGSQCTYVDSISNSGVAWHTT

WTWSGGDNQVKSYANSQVSLTKKLVSQISSIPTTVQWSYDNTNTRADV

AYDLFTAADPNHVTYSGDYELMIWLARYGNVQPIGSQIASVNIGGHNW

ELWYGGSTQKTYSFVSATPITSFSGNVMDFWNYLTRNHGYPASSQYLI

NMQFGTEPFTGGPATLTVSQVVTASVN

Amino acid sequence of the predicted CEL12A mature polypeptide of *Aspergillus fumigatus*.

A comparative pairwise global alignment of amino acid sequences was determined using the Needleman-Wunsch algorithm (Needleman and Wunsch, 1970, *J. Mol. Biol.* 48: 443-453) as implemented in the Needle program of EMBOSS with gap open penalty of 10, gap extension penalty of 0.5, and the EBLOSUM62 matrix. The alignment showed that the deduced amino acid sequence of the *Aspergillus fumigatus* gene encoding the CEL12A mature polypeptide shared 99.5%, 72.9%, and 70.2% identity (excluding gaps) to the deduced amino acid sequences of glycosyl hydrolase family 12 proteins from *Aspergillus fumigatus* (accession number Q4WGT4), *Aspergillus aculeatus* (P22669), and *Aspergillus kawachii* (Q8NJY2), respectively.

Example 3

Expression of the *Aspergillus fumigatus* cel12A Endoglucanase Gene in *Aspergillus oryzae* JaL250

*Aspergillus oryzae* JaL250 protoplasts were prepared according to the method of Christensen et al., 1988, *Bio/Technology* 6: 1419-1422. Five µg of pJZhAfum12A was used to transform *Aspergillus oryzae* JaL250.

The transformation of *Aspergillus oryzae* JaL250 with pJZhAfum12A yielded about 20 transformants. Eight transformants were isolated to individual PDA plates.

Confluent PDA plates of five of the eight transformants were washed with 5 ml of 0.01% TWEEN® 20 and inoculated separately into 25 ml of MDU2BP medium in 125 ml glass shake flasks and incubated at 34° C., 250 rpm. Five days after incubation, 0.5 µl of supernatant from each culture was analyzed using 8-16% Tris-Glycine SDS-PAGE gels (Invitrogen, Carlsbad, Calif., USA) according to the manufacturer's instructions. SDS-PAGE profiles of the cultures showed that one of the transformants (designated *Aspergillus oryzae* JaL250JZhAf12A) secreted a major band of approximately 24 kDa.

Protein for further characterization was generated from *Aspergillus oryzae* JaL250JZhAf12A as described in EP0489718.

Example 4

*Aspergillus oryzae* Genomic DNA Extraction

*Aspergillus oryzae* strain JaL250JZhAf12A expressing the CEL12A protein of *Aspergillus fumigatus* was grown in YEG medium, in 50 ml culture volume, using a baffled shake flask for 2 days, 34° C., at 200 rpm. Biomass was frozen in liquid nitrogen and ground to a powder with a mortar and pestle. The powder was suspended in 15 ml of 0.1 M CAPS-NaOH pH 11.0, 1 mM EDTA, 0.5% lithium dodecyl sulfate and incubated for 60 minutes at 60° C. with periodic mixing by inversion. An equal volume of neutralized phenol was added and the tube was shaken gently for 1 hr at 37° C. 5 ml of chloroform was added and the tube was agitated vigorously for 1 minute. After centrifugation at 1300×g for 10 minutes, the top aqueous phase was re-extracted with an equal volume of phenol:chloroform (1:1) by agitation for 5 minutes. Centrifugation was repeated and the aqueous phase was brought to 2.5 M ammonium acetate and stored at −20° C. for 20 minutes. After centrifugation at 17,000×g for 20 minutes at 4° C., the supernatant nucleic acids in the supernatant were precipitated by adding 0.7 volumes of isopropanol. After centrifugation at 17,000×g for 10 minutes, the supernatant was decanted and the pellet was rinsed with 70% ethanol and air dried. The pellet was dissolved in 950 µl of deionized water followed by addition of 50 µl of Promega Cell Resuspension Solution (Promega Corporation, Madison Wis., USA) and incubation for 5 minutes at room temperature. Ammonium acetate was added to 1.0 M and nucleic acids precipitated by addition of 2 volumes of ethanol. After centrifugation at 13,000×g for 10 minutes, the pellet was dissolved in 300 µl of 1 mM Tris-HCl, 0.1 mM EDTA, pH 8.0, and stored at −20° C.

Example 5

PCR Amplification of the *Aspergillus fumigatus* cel12A Genomic DNA from Genomic DNA of *Aspergillus oryzae* Expression Strain JaL250JZhAf12A For purposes of sequencing and clone deposit, the cel12a DNA was amplified from *Aspergillus oryzae* strain JaL250JZhAf12A genomic DNA. Two synthetic oligonucleotide primers homologous to pJZhAfum12A expression vector were designed to PCR amplify the cel12a gene from *Aspergillus oryzae* strain JaL250JZhAf12A genomic DNA.

```
Forward primer:
5' ccacacttctcttccttcctc 3'    (SEQ ID NO: 5)

Reverse primer:
5' CCCCATCCTTTAACTATAGCG 3'    (SEQ ID NO: 6)
```

Thirty-three picomoles of each of the primers above were used in a PCR reaction containing approximately 300 ng of *Aspergillus oryzae* JaL250JZhAf12A genomic DNA (prepared as described in Example 4), 1×Pfx Amplification Buffer (Invitrogen, Carlsbad Calif., USA), 1.7 µl of a 10 mM blend of dATP, dTTP, dGTP, and dCTP, 2.5 units of Platinum Pfx DNA Polymerase (Invitrogen, Carlsbad Calif., USA), and 1 µl of 50 mM MgSO4 in a final volume of 30 Amplification was performed in a Stratagene Robocycler programmed for 1 cycle at 96° C. for 3 minutes and 72° C. for 3 minutes (during which DNA polymerase was added); and 35 cycles each at 94° C. for 50 seconds, 56° C. for 50 seconds, and 68° C. for 60 seconds, followed by a final extension at 68° C. for 7 minutes.

The reaction products were isolated on a 1.2% agarose gel using TAE buffer where a 0.9 kbp product band was excised from the gel and purified using a QIAEX® II Gel Extraction Kit according to the manufacturer's instructions.

The fragment was cloned into the pCR®4Blunt-TOPO® vector using a Zero Blunt TOPO PCR Cloning Kit and transformed into *E. coli* TOP10 cells according to the manufacturer's instructions (Invitrogen, Carlsbad Calif., USA). Plasmid DNA from several transformants was prepared using a QIAGEN BioRobot 9600. Plasmid from one transformant was sequenced and found to contain the cel12a DNA. The plasmid was designated pPH53.

*E. coli* PaHa53 containing plasmid pPH53 was deposited with the Agricultural Research Service Patent Culture Collection, Northern Regional Research Center, 1815 University Street, Peoria, Ill., 61604, as NRRL #: B-30984, with a deposit date of 8 Nov. 2006.

Example 6

Denim Abrasion with *Aspergillus fumigatus* Cel12A (as Obtained in Example 3) in LOM The characteristics of the *Aspergillus fumigatus* CEL12A (hereinafter refers to AfCEL12A) in denim abrasion, including the temperature profile and pH profile were determined in Launder-O-Meter (SDL-Atlas LP2). Buffers used with different pH including: pH 4.5 (50 mM acetate buffer, 2.93 g of NaAc.3H$_2$O and 1.71 g HAc were dissolved in 1 liter de-ionized water), pH 5.5 (50 mM Acetate buffer, 6.02 g of NaAc.3H$_2$O and 0.35 g HAc were dissolved in 1 L de-ionized water), pH 6.5 (50 mM phosphate buffer, 5.64 g of Na$_2$HPO$_4$.12H$_2$O and 5.34 g of NaH$_2$PO$_4$.2H$_2$O were dissolved in 1 liter de-ionized water), pH 7.5 (50 mM phosphate buffer, 15.05 g of Na$_2$HPO$_4$.12H$_2$O and 1.25 g of NaH$_2$PO$_4$.2H$_2$O were dissolved in 1 liter de-ionized water), pH 8.5 (50 mM phosphate buffer, 17.61 g of Na$_2$HPO$_4$.12H$_2$O and 0.116 g of KH$_2$PO$_4$ were dissolved in 1 liter de-ionized water). The enzymatic treating time was 2 hours, and the temperatures were 25° C., 3° C., 40° C., 50° C., 60° C. respectively. The results were compared with *Trichoderma reesei* CEL12 (Super GX from Genencor).

Raw denim was desized and cut to 12.5 cm tall and 23 cm long. The denim was serged and sewn, forming a tube with height of 12.5 cm and weight of about 13.5 g. The tubes were placed in the conditioned room (65% humidity, 20° C.) for 24 hours before they were numbered, weighed by the analytical balance and recorded. One conditioned tube was placed in each beaker, with the blue side facing inward. For each beaker, 30 big nuts (M6M-SR-A4-80, acid proof), 10 small nuts (M6M-SR-A4-80, acid proof), 7 big star magnets (diam. 17 mm, item no. 3-CO-411117, Cowie, Schweiz via Bie & Berntsen, and 3 small star magnets (diam. 14 mm, item no. 3-00-11117, Cowie, Schweiz via Bie & Berntsen) were used to supply the mechanical aids. Then the buffers were added based on the calculation of enzyme solutions, the total volume was 200 ml, which would create a liquid ratio about 15:1.

The LOM machine was started after the required program was chosen, and it would hold when the temperature reached the set one. After that, 54 mg/L of Af CEL12A were added to beakers containing different pH buffers respectively, 2 beakers for each pH. For each pH, two beakers containing no enzymes were used as the blank control. Two beakers containing 54 mg/L of *Trichoderma reesei* CEL12 (protein purified from the formulated Super GX granule, hereinafter refers to Tr CEL12), and/or two with addition of formulated Super GX granule to give a concentration of Tr CEL12 protein to 54 mg/L at pH 5.5, were used for comparison. Fitted each beaker with a lid lined with 2 neoprin gaskets and close, e.g., with the metal clamping device. Loaded the beakers into the preheated LOM. Metal racks were used to accommodate and secure 6 beakers, in the horizontal position, in each of the 4 drum positions. Closed the LOM lid and continued the washing program. 2 hours later, removed all beakers and transferred the denim samples to the inactivation solution (2 g/L sodium carbonate) at 85° C. for 10 minutes. Then the swatches were rinsed in hot water 2 times and in cold water 2 times. Tumble-dried the denim samples, and conditioned the samples for 24 hours at 20° C., 65% R. H prior to evaluation.

The abrasion level and backstaining level of the denim samples were determined by measuring the reflectance with pre-calibrated DataColor SF450X. Four readings were taken for each sample. The abrasion level was evaluated with the index CIE L* of the blue side of the sample, and the backstaining level was evaluated with the index CIE b* of the back of the sample.

Figure 2:
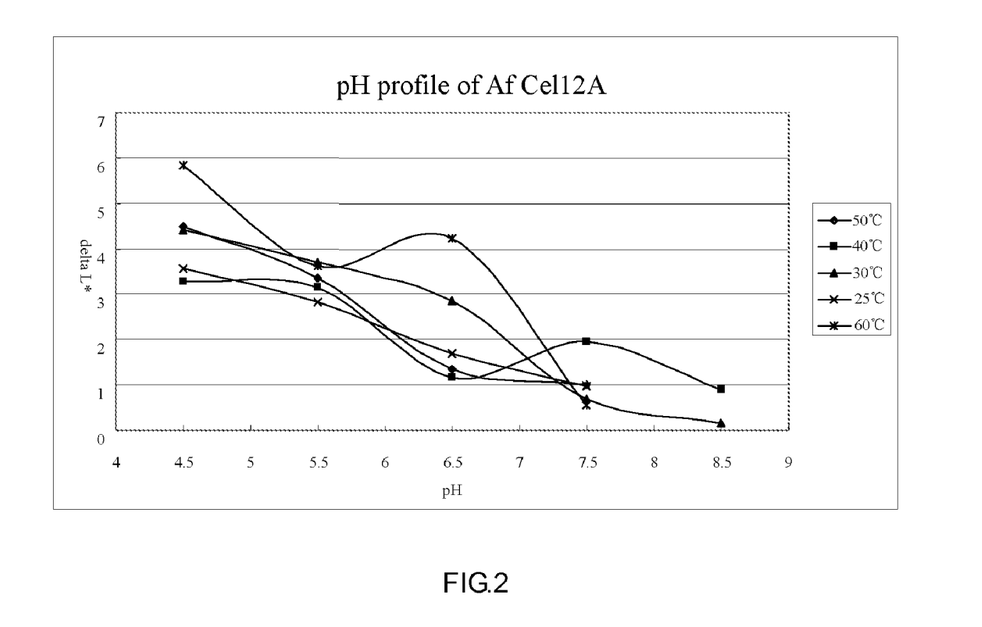
FIG. 2 describes the pH profile of *Aspergillus fumigatus* CEL12A endoglucanase in denim abrasion at different temperature.

As shown in FIG. 2, the abrasion level (represented by delta L*, delta L*=L* of the swatch treated with a certain cellulase-L* of the swatch treated in the same condition but without cellulases) changed with the pH values of the buffers at all the tested temperatures. This pH profile suggested that Af CEL12A performed quite well in buffers with pH between 4.5 and 5.5, revealing its preference towards an acid buffer.

Figure 3:
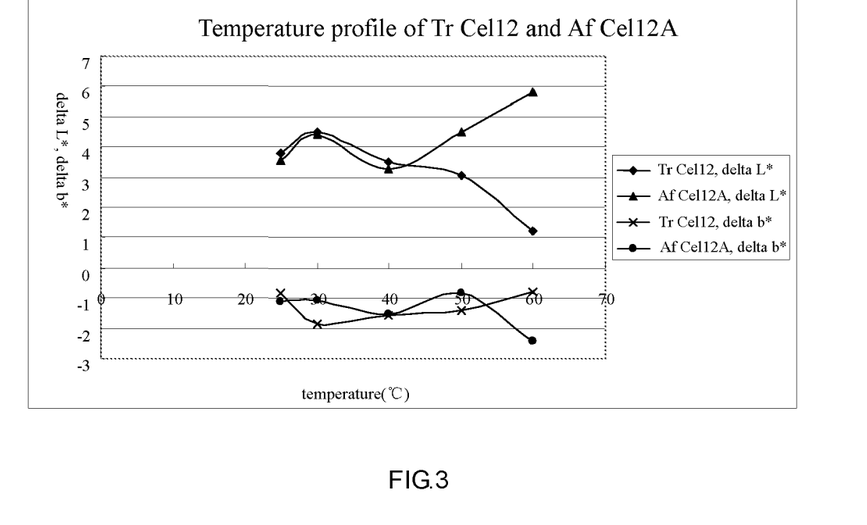
FIG. 3 describes the temperature profile of *Trichoderma reesei* CEL12 at pH 5.5 and *Aspergillus fumigatus* CEL12A endoglucanase at pH 4.5.

As shown in FIG. 3, the abrasion levels and backstaining levels (represented by delta L* and delta b* respectively, the definition of delta L* as above, delta b*=b* of the swatch treated with a certain cellulase−b* of the swatch treated in the same condition but without cellulases) by different cellulases were plotted versus temperatures. It could be observed that Af CEL12A could be applied in a broad temperature range from about 25° C. to 60° C. To get a similar abrasion level, Af CEL12A would cause significant lower backstaining level than Tr CEL12 protein purified from Super GX.

For trials at 25° C. and 60° C., commercial product of Tr CEL12 (Super GX) was used, and for other temperatures, Tr CEL12 purified from formulated commercial products Super GX were used instead.

Example 7

Bio-Polishing by Af CEL12A

The characteristics of the Af CEL12A in bio-polishing, including the temperature profile and dosage profile were determined in Launder-O-Meter. The results were compared with CELLUCLAST® proteins and Super GX (from Genencor).

Knitted interlock fabric, 100% cotton or Test Fabric Style 460, were cut into 16.5 cm* 16.5 cm, as the standard swatches. The swatches were placed in the conditioned room (65% humidity, 20° C.) for 24 hours before they were numbered, weighed by the analytical balance and recorded. Two conditioned swatches were placed in each beaker. For each beaker, 20 big steel balls in each beaker (220 g) were used to supply the mechanical aids. Then the buffers (50 mM acetate buffer, pH 5.0) were added based on the calculation of enzyme solutions, the total volume was 100 ml, which would create a liquid ratio about 10:1.

The LOM machine was started after the required program was chosen, and it would hold when the temperature reached the set one. For each trials with temperatures 30° C., 40° C., 50° C., 55° C. and 60° C., two beakers contained 30 mg/L of Af CEL12A, two beakers contained 36 mg/L of Af CEL12A, two beakers containing 36 mg/L of Super GX proteins and 143 mg/L of CELLUCLAST® proteins respectively were used as the benchmark, two beakers containing no enzymes were used as the blank control. Seal up the beakers and place them in the LOM, and start the enzymatic treatment in LOM for 1 hour. When time was up, remove all beakers and transfer the swatches to the inactivation solution (2 g/L sodium carbonate) at 85° C. for 10 minutes. Then the swatches were rinsed in hot water 2 times and in cold water 2 times. Tumble-dried these samples, and conditioned the samples for 24 hours at 20° C., 65% R. H prior to evaluation.

For each treating condition, there were 4 swatches. They were weighed and recorded to get the weight loss data. 1 swatch was used for the pilling notes test with Martindale pilling tester, and the other 3 swatches were used for the burst strength test with Burst Strength Tester to get the strength loss data.

Figure 4:
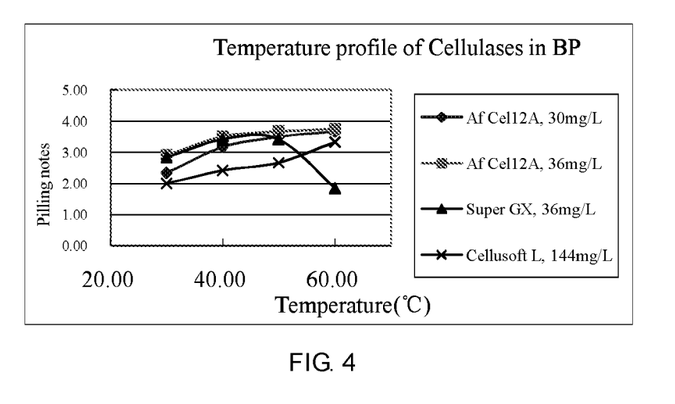
FIG. 4 describes the temperature profile of *Aspergillus fumigatus* CEL12A endoglucanase, Super GX and Cellusoft L in bio-polishing from 30° C. to 60° C.
Figure 5:
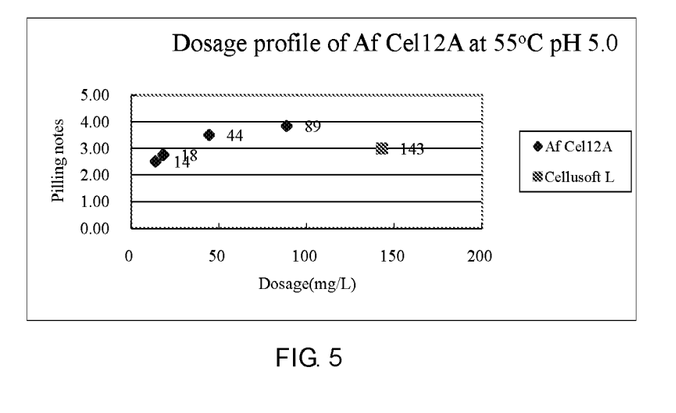
FIG. 5 describes the dosage profile of *Aspergillus fumigatus* CEL12A endoglucanase at 55° C. pH 5.0.

As shown in FIG. 4, Af CEL12A could reduce pilling formation in a temperature range from 30° C. to 60° C., which was broader than that of CELLUCLAST® proteins (effective when higher than 50° C.) and Super GX protein (effective when lower than 50° C.).

As shown in FIG. 5, 18-44 mg/L Af CEL12A was comparable to 143 mg/L Cellusoft L in anti-pilling performance, which meant Af CEL12A was 3-4 times stronger than celluclast proteins in bio-polishing at pH 5.0, 55° C.

Figure 6:
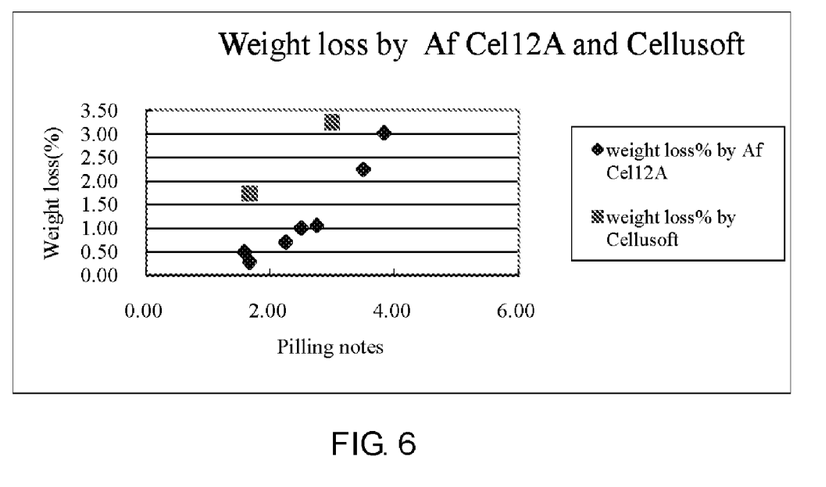
FIG. 6 describes the weight loss caused by *Aspergillus fumigatus* CEL12A endoglucanase and CELLUSOFT® L.

As shown in FIG. 6, to gain the same anti-pilling level, the weight loss caused by Af CEL12A was much lower than that caused by CELLUCLAST® proteins.

As shown in Table 1, Af CEL12A and Super GX could cause almost the same anti-pilling effects form 30° C. to 50° C. at the same protein load. While Af CEL12A showed a slight superiority over Super GX in terms of strength loss.

TABLE 1

Bio-Polishing performance comparison between Af CEL12A and Super GX

| Enzyme | Strength loss(%) | Pilling notes |
| --- | --- | --- |
| Af CEL12A (30 mg/L) | 10.73 | 3.50 |
| Af CEL12A (36 mg/L) | 12.85 | 3.75 |
| Super GX (36 mg/L) | 16.83 | 3.50 |

The invention claimed is:

1. A method of forming localized variation of color density in the surface of a dyed cellulosic fabric, comprising contacting said fabric with a composition comprising a cellulase which has at least 95% sequence identity with SEQ ID NO:2.

2. The method of claim 1, wherein the fabric is indigo dyed denim.

3. The method of claim 1, wherein the cellulase is a cellulase of family 12.

4. The method of claim 1, wherein the cellulase is derived from *Aspergillus*.

5. The method of claim 1, wherein the cellulase is derived from *Aspergillus fumigatus*.

6. The method of claim 1, wherein the cellulase comprises the amino acid sequence of SEQ ID NO:2.

7. A method for reducing back-staining during the stonewashing of colored fabrics which method comprises contacting the fabrics with a composition comprising a cellulase which has at least 95% sequence identity with SEQ ID NO:2.

8. The method of claim 7 wherein the fabric is indigo dyed denim.

9. The method of claim 7, wherein the cellulase is a cellulase of family 12.

10. The method of claim 7, wherein the cellulase is derived from *Aspergillus*.

11. The method of claim 7, wherein the cellulase is derived from *Aspergillus fumigatus*.

12. The method of claim 7, wherein said composition further comprises a surfactant.

13. A method for biopolishing a cellulose-containing fabric, said method comprising contacting said fabrics with an aqueous bulk solution containing a composition comprising a cellulase which has at least 95% sequence identity with SEQ ID NO:2.

14. The method of claim 13, wherein the cellulose-containing fabric comprises a cellulosic fiber selected from the group consisting of cotton, flax, ramie, hemp, jute, rayon, lyocell, and combinations of any of the foregoing with each other or with a non-cellulosic fiber.

15. The method of claim 13, wherein the cellulase is derived from *Aspergillus*.

16. The method of claim 13, wherein the cellulase is derived from *Aspergillus fumigatus*.

17. The method of claim 13, wherein said biopolishing is characterized by the improved property selected from the group consisting of pilling note, handle, and appearance.

18. The method of claim 13, wherein said bulk solution further comprises an enzyme or enzymes selected from the group consisting of proteases, cutinases, amylases, pectin-digesting enzymes, and hemicellulases.

* * * * *